United States Patent [19]
Couche et al.

[11] Patent Number: 5,222,480
[45] Date of Patent: Jun. 29, 1993

[54] DEFIBRILLATOR DISCHARGE CALIBRATION SYSTEM

[75] Inventors: Charles. Couche, Seattle; Walter A. I. Taylor, Renton, both of Wash.

[73] Assignee: Physio-Control Corporation, Redmond, Wash.

[21] Appl. No.: 600,250

[22] Filed: Oct. 18, 1990

Related U.S. Application Data

[63] Continuation of Ser. No. 292,186, Dec. 30, 1988, abandoned.

[51] Int. Cl.⁵ .............................................. A61N 1/36
[52] U.S. Cl. ........................... 128/419 D; 128/419 PS
[58] Field of Search .......... 128/419 D, 419 R, 419 PS

[56] References Cited

U.S. PATENT DOCUMENTS

| | | | |
|---|---|---|---|
| 3,442,269 | 5/1969 | Druz | 128/419 D |
| 3,513,850 | 5/1970 | Weber | 128/419 D |
| 3,787,767 | 1/1974 | Hammer et al. | 128/419 D |
| 3,798,542 | 3/1974 | Dempsey | 128/419 D |
| 3,860,009 | 1/1975 | Bell et al. | 128/419 D |
| 3,862,636 | 1/1975 | Bell et al. | 128/419 D |
| 3,886,950 | 6/1975 | Ukkestad et al. | 128/419 D |
| 4,094,310 | 6/1978 | McEachern et al. | 128/419 D |
| 4,328,808 | 5/1982 | Charbonnier et al. | 128/419 D |
| 4,693,253 | 9/1987 | Adams | 128/419 D |
| 4,771,781 | 9/1988 | Lerman | 128/419 D |
| 4,823,796 | 4/1989 | Benson | 128/419 D |

OTHER PUBLICATIONS

Jones, V. C. et al., "Determining transthoracic impedance, delivered energy, and peak current during defibrillation episodes," Medical Instrumentation, vol. 15, No. 6, Nov.-Dec. 1981.

Kerber, R. E. et al., "Automated impedance-based energy adjustment for defibrillation: experimental studies," Circulation, vol. 71, No. 1, Jan. 1985, pp. 136-140.

Primary Examiner—Kyle L. Howell
Assistant Examiner—George Manuel
Attorney, Agent, or Firm—Christensen, O'Connor, Johnson & Kindness

[57] ABSTRACT

A defibrillator (10) is disclosed in which measured information concerning the energy delivered by the defibrillator to a meter (56) is employed to calibrate subsequent discharges by the defibrillator at the same energy level. In connection with that process, a microprocessor (70) controls the operation of a feedback loop (50), including a controlled-gain amplifier (64), level detector (66), adder (68) and energy charger (58), to adjust the voltage applied to a discharge capacitor (54) in response to the energy measured by the meter. The information can be input to the microprocessor either manually or automatically and can be used by the microprocessor in performing a piecewise linear approximation of the voltage adjustment required to deliver the desired nominal energy, or in performing a direct computation of that adjustment. This process is repeated for each of the energy levels selectively dischargeable by the defibrillator.

10 Claims, 3 Drawing Sheets

DEFIBRILLATOR DISCHARGE CALIBRATION SYSTEM

This application is a continuation application based on prior copending application Ser. No. 292,186, filed on Dec. 30, 1988 now abandoned.

FIELD OF THE INVENTION

This invention relates generally to defibrillators and, more particularly, to the calibration of defibrillators.

BACKGROUND OF THE INVENTION

The heart is the central element of the cardiovascular system and includes four chambers known as the left and right atria and left and right ventricles. Venous blood from the body is received by the right atrium and passed to the right ventricle, where it is pumped to the lungs via the pulmonary artery. Once oxygenated, this blood returns to the left atrium and is pumped to the aorta, by contraction of the left ventricle, for circulation throughout the body.

The operation of the heart is the result of muscular contractions of the chambers induced by electrical impulses. A sinoatrial node is the normal pacemaker of the heart and produces on the order of 50 to 80 of these electrical impulses per minute. Each impulse travels first across the atria and then across the ventricles, causing the atrial and ventricular muscle fibers to sequentially contract. After contraction, these muscle fibers repolarize and return to a resting state in preparation for the next electrical impulse.

Proper operation of the cardiovascular system is thus dependent upon the operation of the sinoatrial node. In certain instances, however, the sinoatrial node continues to operate properly but the heart experiences an arrhythmia or irregularity that affects the ability of the muscle fiber to properly respond to the impulses produced by the sinoatrial node. The most serious form of arrhythmia is known as "ventricular fibrillation."

Ventricular fibrillation is a potentially fatal condition caused by uncoordinated electrical impulses that produce twitching of individual ventricular muscle fibers with little or no contraction of the ventricles as a whole. The heart is, thus, unable to transport blood and, with it, oxygen to the various parts of the patient's body. Ventricular fibrillation may be induced by physiological phenomena, such as coronary disease and myocardial infraction, as well as environmental phenomena, including electric shock, drug toxocity, and drowing. The heart is particularly susceptible to ventricular fibrillation during repolarization of the ventricular muscle fiber.

Defibrillation involves the delivery of electric energy to the heart, either directly through an open chest or indirectly through the chest wall, to terminate ventricular fibrillation. The defibrillation energy must be sufficient to depolarize a relatively large section of the muscle fiber and, once removed, allow the sinoatrial node to resume pacing of the heart. The energy required to accomplish this depends on a number of factors including, for example, the size of the patient.

Although distinguished in severity from ventricular fibrillation, a number of other arrhythmias may be experienced by the heart. For example, atrial fibrillation and atrial and junctional tachycardias may occur, disrupting proper operation of the heart. Because some blood is still pumped by the heart, however, these conditions are not as serious as ventricular fibrillation. In fact, the application of electric energy to the heart to terminate these conditions may even be elective. In any event, however, energy should not be applied to the heart during the vulnerable period of ventricular repolarization, or the more severe condition of ventricular fibrillation may be induced.

The termination of irregularities other than ventricular fibrillation is commonly referred to as synchronized cardioversion, rather than defibrillation. Synchronized cardioversion typically involves the application of a lower level of energy to the heart during a select portion of the ECG waveform other than the vulnerable period of ventricular repolarization. For the purposes of this application, however, the term "defibrillation" will be understood to include the application of energy to the heart to terminate ventricular fibrillation, as well as other arrhythmia and irregularities traditionally considered to be the subject of synchronized cardioversion.

Addressing the prior art of defibrillation, conventional defibrillators store energy for discharge, for example, through a pair of paddle electrodes positioned on the patient's chest. Upon discharge, a brief pulse of energy is applied to the patient's heart, repolarizing the heart's muscle fiber and allowing the sinoatrial node to reinitiate proper pacing in the manner described above. Typically, the operator is free to select from any one of a plurality of energy discharge levels, depending upon a number of characteristics, including, for example, the size of the patient and the type of irregularity experienced by the heart.

As will be appreciated, proper control of the level of energy applied to the patient's heart is important to successful defibrillation. For example, if the energy discharged by the defibrillator is less than that desired by the operator, the discharge may be unsuccessful in terminating the irregular operation of the heart. Although a subsequent discharge at a higher energy level can still be employed, even momentary delays in the restoration of proper circulation can significantly increase the damage suffered by certain of the patient's organs, such as the brain. The patient may also be injured if the energy discharged by the defibrillator is greater than expected. In that regard, an extremely high discharge may damage the muscle fiber of the heart, impairing its operation. In addition, an unexpectedly high discharge applied to correct a mild arrhythmia or irregularity might possibly induce a more serious, ventricular fibrillation.

Several approaches have been adopted in the past to control defibrillation discharge levels. For example, in U.S. Pat. Nos. 3,860,009 (Bell et al.), 3,862,636 (Bell et al.), and 3,886,950 (Ukkestad et al.), defibrillators are disclosed in which the operator selects the desired level of energy to be discharged to the patient. Basically, these defibrillators employ information concerning the voltage and current applied to the patient by a storage capacitor, along with the interval of time that they applied, to compute the energy transferred. In that regard, the conventional unit of energy is the joule, with one joule being equal to the energy provided by a one-volt potential and one-ampere current for one second. Thus, by measuring the voltage and current and controlling the duration of their application to the patient, the defibrillators disclosed in these patents are able to control the energy transferred to the patient.

This general approach, however, relies upon information about the voltage or current that may be somewhat inaccurate. More particularly, the accuracy of the voltage, current, and time measurements may vary from one defibrillator to the next or for the same defibrillator over an interval of time. Thus, although such prior art defibrillators do attempt to control discharges of energy, they do not address the need for defibrillator calibration to ensure that the computed energy discharge actually corresponds to the desired energy discharge.

In another prior art arrangement, an energy level selection switch is employed to selectively allow different resistors to be switched into a voltage divider formed with a first variable resistor placed across an energy storage capacitor. By selectively switching a particular resistance into the divider, the voltage applied to the capacitor and, hence, the energy stored for discharge, can be controlled. The variable resistor can also be adjusted to proportionally increase or decrease the voltage applied to, and energy stored by, the capacitor at each energy level.

A plurality of displays are also employed by this arrangement to indicate the particular energy level selected. More particularly, another voltage divider is employed to produce a plurality of reference voltages for use by comparators in controlling the operation of the displays. These comparators compare the voltage applied to the capacitor with one or more reference voltages to ensure that the applied voltage is within the range required to provide the desired energy storage and discharge. A second variable resistor common to each leg of this voltage divider allows the reference voltages input to the comparators to be adjusted so that the relationship between the capacitor voltages and the activation of a particular display can be controlled.

Although the adjustment of either of the variable resistors noted above represents a calibration, some improvement can still be made in the calibration of the defibrillator. For example, it would be desirable if calibration of the defibrillation discharge could be accomplished separately for each discharge level, rather than via a single adjustment that affects each level simultaneously. Such an approach would avoid the necessity of repeating the calibration performed for previous levels when an adjustment is made in a subsequent energy level calibration. It would also be desirable if the calibration procedure could be performed on the basis of the energy actually discharged rather than on parameters such as the voltage applied to the capacitor to develop a stored charge.

SUMMARY OF THE INVENTION

In accordance with this invention, a method and apparatus for calibrating a defibrillator are disclosed. Briefly, data concerning an actual discharge of energy at a select discharge level is employed to control subsequent discharges at the same level to improve the accuracy of the discharges. This process is then repeated for each of the discharge levels that can be selected by the operator.

In accordance with a particular aspect of the invention, a defibrillator is disclosed for discharging energy to a patient. The defibrillator includes an input device for allowing a measurement of the energy to be input to the defibrillator. A control device is further included for controlling the discharge of energy in response to the measurement of energy input to the defibrillator. A device for selecting one of a plurality of energy levels for discharge by the defibrillator may also be employed along with a display device for producing a display of the one of the plurality of energy levels selected.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT OF THE INVENTION

Figure 1:
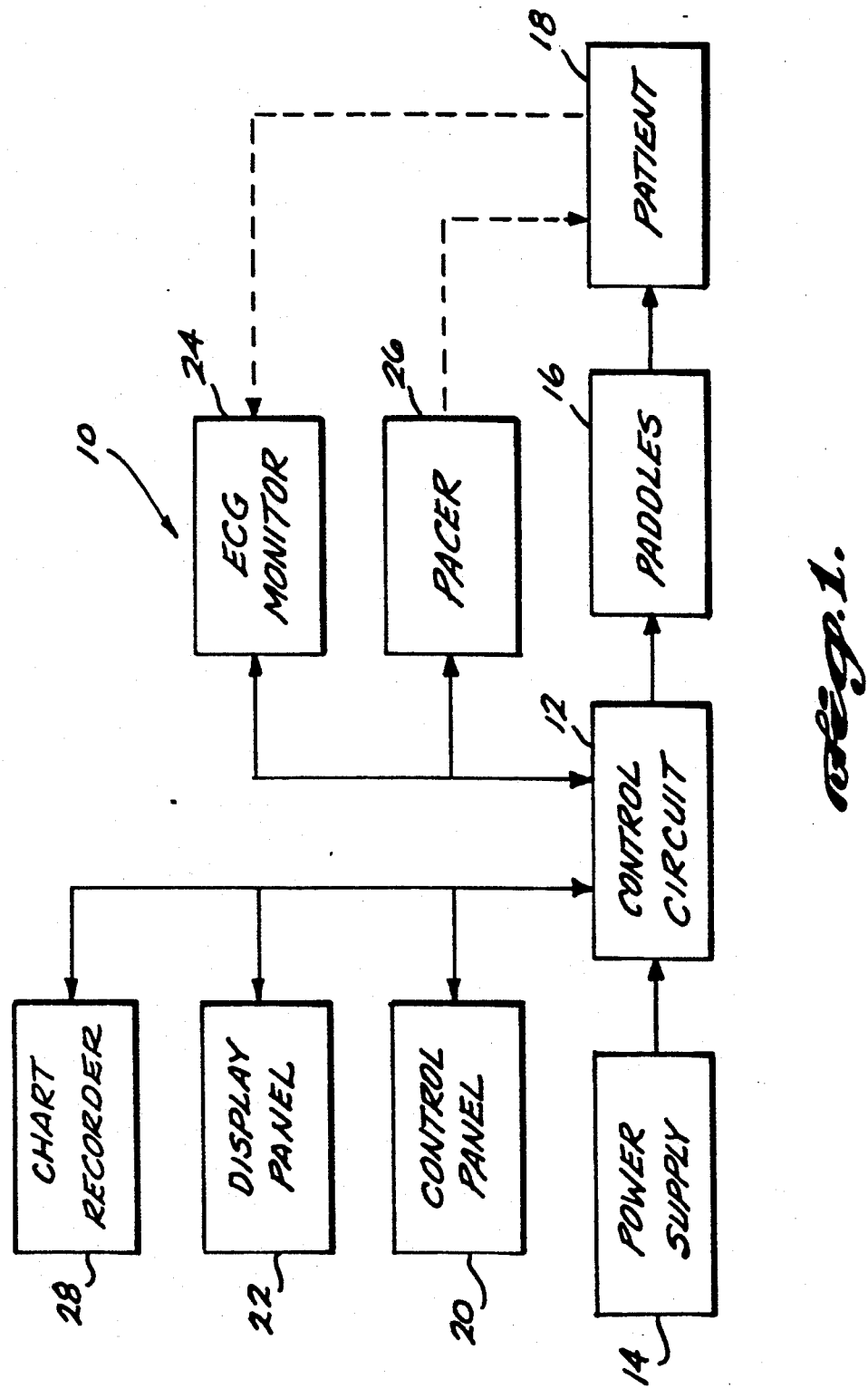
FIG. 1 is a block diagram of a defibrillator constructed in accordance with this invention.

Referring now to FIG. 1, a block diagram of a defibrillator 10 constructed in accordance with this invention is shown. As noted previously, the purpose of defibrillator 10 is to allow an operator to provide a brief (for example, 5- to 30-millisecond) pulse of energy to a patient's heart to terminate irregularities such as ventricular fibrillation and allow repolarization of the muscle fibers so that the sinoatrial mode can restore the heart to proper operation. The disclosed defibrillator 10 is designed to allow the operator to quickly and accurately calibrate the discharge of energy at any of a plurality of levels.

Before discussing the details of defibrillator 10, some general comments concerning the energy produced by defibrillator 10 are provided. For example, the energy stored by defibrillator 10 for discharge to the heart may be different from the energy delivered by defibrillator 10. As noted above, electrical energy is the product of voltage, current, and time and is measured in units known as joules. Thus, if the voltage stored on the capacitor is reduced before reaching the patient, the energy delivered by the defibrillator 10 will be less than that stored. The delivered energy is typically considered to be an average energy that would be delivered through a 50-ohm test load and is often on the order of 50 to 80 percent of the stored energy as the result of losses inherent in defibrillator 10 as well as the resistance to current flow at the skin-defibrillator interface. For the purposes of the ensuing discussion, references to discharged energy will be considered to be the delivered energy for a reference load impedance corresponding to that of the metering equipment used.

Addressing now the various components of defibrillator 10 in greater detail, as shown in FIG. 1, defibrillator 10 includes a control circuit 12 that allows the operator to select one of a group of accurate levels of energy to be transferred from a power supply 14 to defibrillator paddles 16 and a patient 18. A control panel 20 provided on the defibrillator 10 includes a plurality of switches that allow data to be input to defibrillator 10. Similarly, a display panel 22 allows the defibrillator 10 to provide information to the operator.

A number of additional components are also commonly included in the same housing and, for the purposes of this disclosure, will be considered as part of defibrillator 10. For example, an electrocardiogram (ECG) monitor 24 includes electrodes attached to patient 18 and circuitry that monitors the electrical activity of the patient's heart. A pacer 26 employs information obtained from the ECG monitor 24 to supplement the operation of a faulty sinoatrial node by applying relatively small, periodic pulses of energy to the patient's heart. Finally, a strip chart recorder 28 may be included to provide a permanent record concerning the discharge of defibrillation energy, and the operation of the ECG monitor 24 and pacer 26.

Addressing several of the components of defibrillator 10 in greater detail, power supply 14 is conventionally designed for connection to a standard 110/120-volt, 50/60 Hz alternating current (AC) outlet. The power supply 14 then converts that AC voltage into a direct current (DC) voltage for use by the remainder of defibrillator 10. Alternatively, power supply 14 may include one or more batteries that directly provide DC voltage to defibrillator 10. The inclusion of batteries is particularly advantageous in units designed for use in emergency medical treatment outside the hospital environment.

As noted previously, energy is discharged to the patient 18, or other load, through paddles 16. The paddles 16 typically include electrodes 30 that are applied to the patient's skin with a layer of electrolytic gel. The electrodes 30 are responsible for transferring energy to the patient 18, typically in response to the closure of at least one discharge switch 32 included on paddles 16. The paddles 16 are normally applied to patient 18 in an anterior-anterior or anterior-posterior arrangement designed to maximize the transfer of energy to the patient's heart.

The control panel 20 includes a plurality of switches that allow defibrillator 10 to be controlled. For example, a power switch 34 allows defibrillator 10 to be turned ON and OFF. A mode switch 36 allows the defibrillator 10 to be operated in various modes including a calibration mode of operation. The control panel 20 also includes an energy select switch 38 that allows the operator to select any one of a plurality of energy levels for application to the patient's heart during defibrillation. The final switches of interest on control panel 20 are nominal energy level increment and decrement switches 40 and 42, respectively. These switches 40 and 42 are used in the calibration mode of operation in a manner described in greater detail below.

Like control panel 20, the display panel 22 includes a plurality of components. For example, a mode of operation display 44 indicates the particular mode that defibrillator 10 is operating in. An energy display 46 indicates the nominal energy to be discharged by defibrillator 10, as selected by switch 38. Finally, the patient's ECG may be provided in real time by an ECG display 48, with markers employed to identify the points at which synchronized pacing and cardioversion or defibrillation pulses are applied to the patient.

Figure 2:
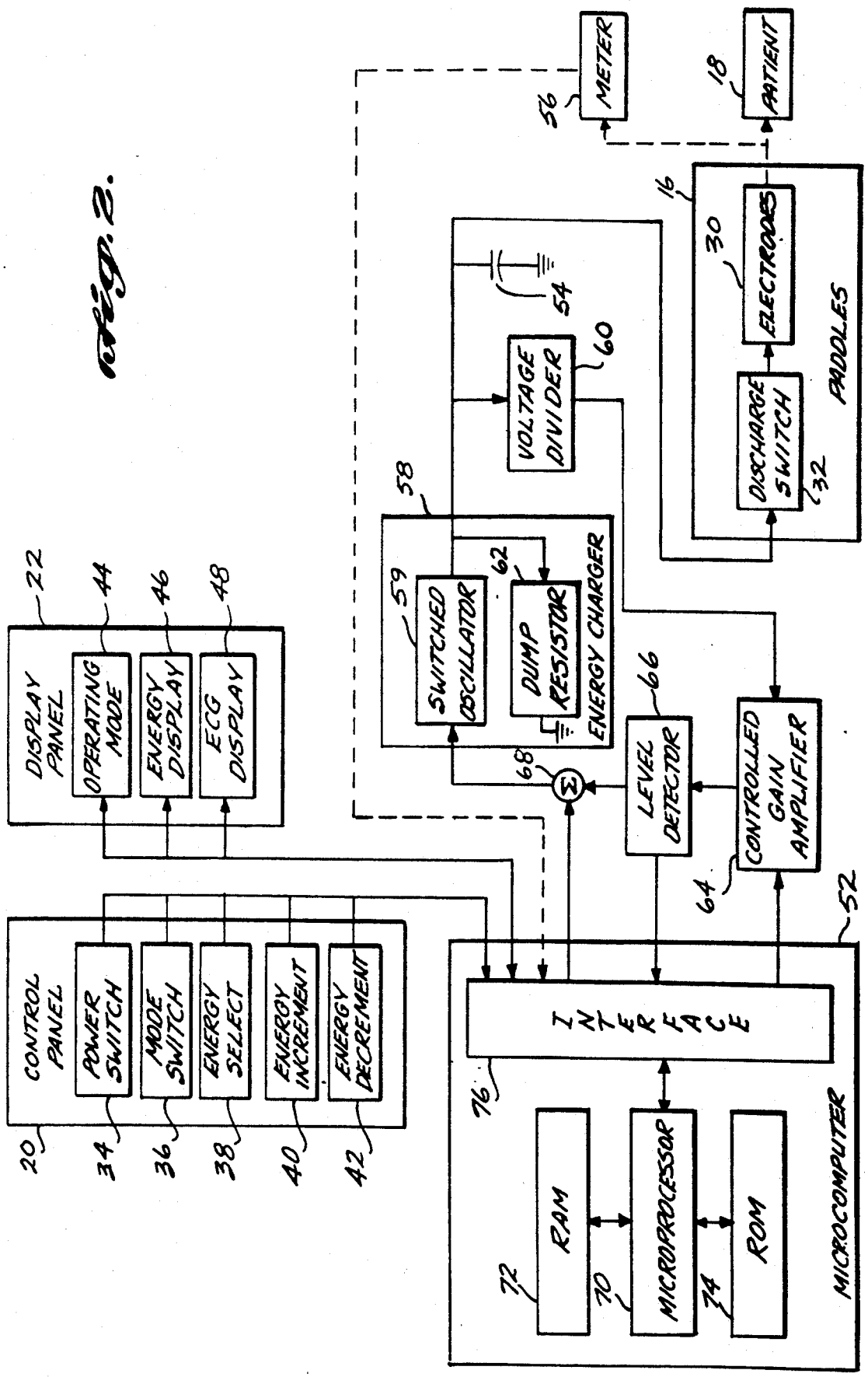
FIG. 2 is a more detailed diagram of the defibrillator of FIG. 1.

Of the various components of defibrillator 10, however, perhaps the most important with respect to the present discussion is the control circuit 12. The circuit 12, as shown in FIG. 2, includes a number of elements. A feedback loop 50 responds to a microcomputer 52 to control and calibrate the energy stored on a defibrillation capacitor 54 for discharge to patient 18. A meter 56, which may either be external to defibrillator 10 or be included as part of the control circuit 12, provides microcomputer 52 with information used in the calibration process.

As noted above, defibrillation capacitor 54 stores the energy to be discharged to the patient. In the preferred arrangement, the capacitor 54 is a 50-microfarad device that can be charged at the rate of 40 joules per second and discharged in roughly 20 seconds by a 100-kilohm, 15-watt load resistor connected in parallel with capacitor 54. Once charged, the capacitor 54 voltage is maintained or refreshed to within approximately ±5 percent of the nominal energy selected for an interval of approximately 60 seconds.

These performance characteristics are partially determined by an energy charger circuit 58, which may include a switched oscillator 59 and dump resistor 62. The switched oscillator 59 is controlled by microcomputer 52 to regulate the intervals during which voltage is applied to capacitor 54. The switched oscillator 59 is kept ON long enough initially to allow the voltage on capacitor 54 to rise to the desired level. As charge decays from capacitor 54 prior to a defibrillation discharge, oscillator 59 is also periodically switched ON to maintain or refresh the desired voltage across capacitor 54. The dump resistor 62 can be switched into the circuit to discharge the energy stored by capacitor 54, if it is not otherwise to be used.

The feedback loop 50 also includes a voltage divider 60, controlled-gain amplifier 64, level detector 66, and summing junction 68 that cooperate with microcomputer 52 to control and calibrate the energy discharged by defibrillator 10 via negative feedback. More particularly, the voltage divider 60 is included to reduce the relatively high voltage stored on capacitor 54 to a level that is suitable for application to the remaining components of the feedback loop 50. Thus, the controlled-gain amplifier 64 has as its input a voltage that is proportional to the voltage across capacitor 54 but reduced by the voltage divider 60. The output of the controlled-gain amplifier 64 is equal to this input voltage, multiplied by the gain $\alpha$ of amplifier 64. The amplifier gain $\alpha$ is in turn controlled by microcomputer 52 in the manner described below.

The level detector 66 is included to monitor the output of amplifier 64. Level detector 66 provides microcomputer 52 with information concerning the magnitude of the amplifier output and also applies the output to summing junction 68. There, the signal applied to summing junction 68 directly from microcomputer 52 is reduced by the amplified output (by virtue of the use of negative feedback), prior to being applied to the energy charger circuit 58 and capacitor 54.

As noted previously, the basic operation of the control circuit 12 and remainder of defibrillator 10 is controlled by microcomputer 52. As shown in FIG. 2, microcomputer 52 includes a microprocessor 70 coupled to a random-access memory (RAM) 72, a read-only memory (ROM) 74, and an interface 76. As will be discussed in greater detail below, ROM 74 includes data and programmed instructions for use by microprocessor 70 in the calibration and operation of defibrillator 10. RAM 72, on the other hand, allows microprocessor 70 to store information developed and used by defibrillator 10 during such procedures. The interface 76 allows microprocessor 70 and the remainder of defibrillator 10 to interact in the desired fashion.

The final component to be discussed is energy meter 56. Energy meter 56 is preferably of the type that reads directly in joules and is intended to measure the energy delivered by defibrillator 10 at the various select energy levels. Although energy meter 78 may or may not be included in defibrillator 10, in the preferred arrangement it is a separate component to reduce the overall cost of defibrillator 10. As shown in FIG. 2, feedback from meter 56 is provided to microcomputer 52 for use in adjusting the gain α of amplifier 64.

Figure 3:
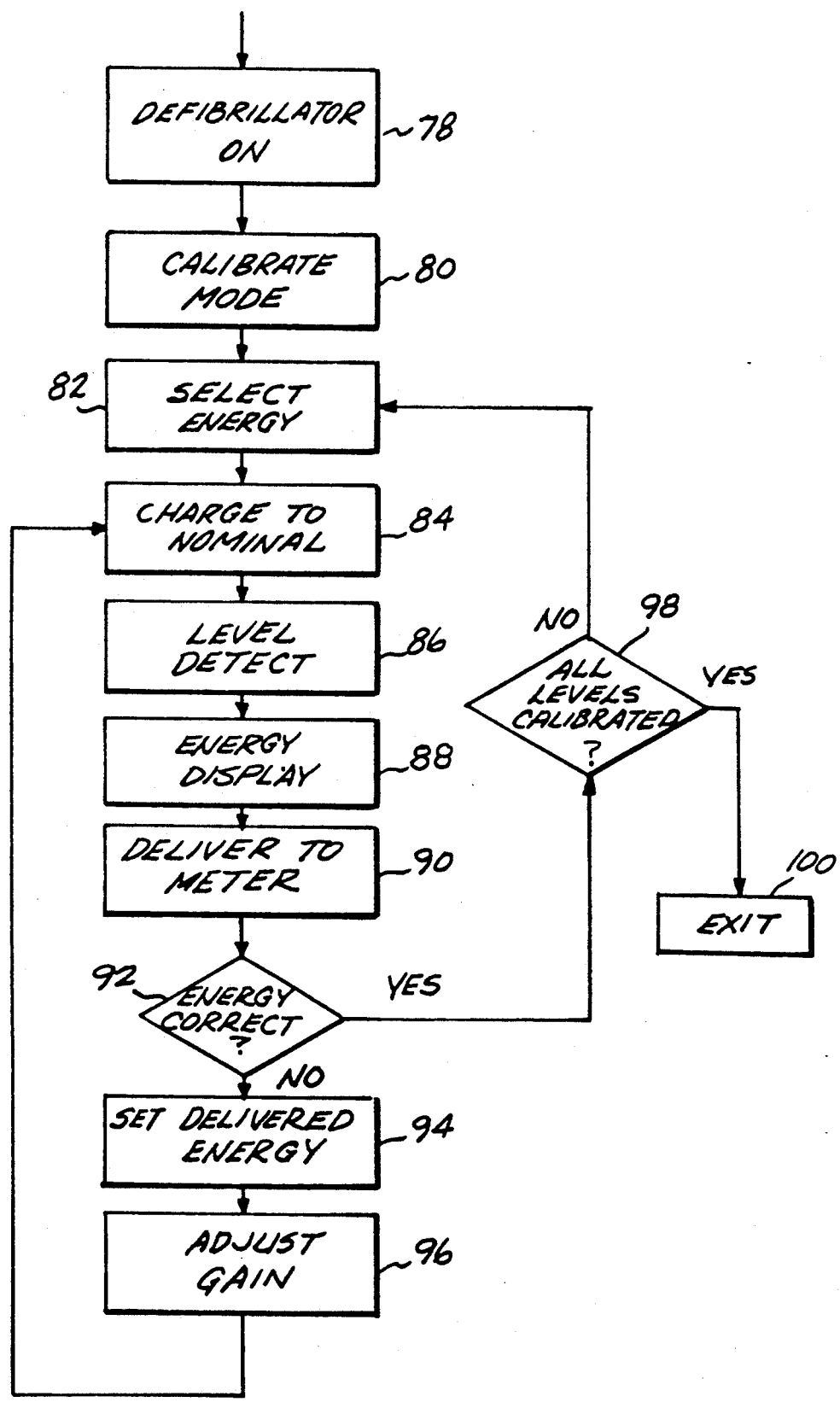
FIG. 3 is a flow chart depicting the operation of a calibration circuit employed by the defibrillator of FIG. 1.

Discussing now the operation of defibrillator 10, reference is had to the flow chart of FIG. 3. As shown, calibration of the defibrillator 10 is typically performed immediately after turning defibrillator 10 on with power switch 34, as represented by the DEFIBRILLATOR ON block 78 of the flow chart. The first step in the calibration process is to place defibrillator 10 in a "calibrate" mode of operation, represented by the CALIBRATE MODE block 80 in FIG. 3. Although the calibrate mode of operation is accessed in the preferred embodiment by the simultaneous depression of switches on control panel 20, for simplicity it can be considered to be accomplished by actuation of a single mode switch 36. The operation of mode switch 36 is passed to microprocessor 70 via interface 76, causing the program instructions in ROM 74 pertaining to calibration of defibrillator 10 to initiate control of microprocessor 70 and initialize the various parameters employed by microprocessor 70 during calibration.

The microprocessor 70, programmed in this manner, first monitors the status of the energy select switch 38 included on control panel 20 to determine the desired energy to be discharged to the patient. This step is represented by the SELECT ENERGY block 82 shown in FIG. 3. Typically, a plurality of energy levels are available for selection including, for example 5, 10, 20, 30, 50, 100, 200, 300, and 360 joules.

In response to the energy level selected, microprocessor 70 provides an output voltage to summing junction 68, a gain adjustment signal to amplifier 64, and a control signal to switching oscillators 59 to charge capacitor 54 to the desired voltage. This process is represented by the CHARGE TO NOMINAL block 84 of FIG. 3. Typically, the output voltage, gain adjustment signal, and control signal produced by microprocessor 70 vary for each different energy level selected by switch 38.

The microprocessor 70 next monitors the output of level detector 66 at the LEVEL DETECT block 86 to ensure that the nominal value of the voltage that is to be applied to capacitor 54 for the particular energy level selected is actually provided. This is accomplished by a comparison of the detected voltage with the nominal voltage value stored in memory for the energy level selected. As will be appreciated, upon power-up, the nominal value is loaded into RAM 72 from ROM 74, while subsequent revisions to the nominal value are stored in RAM 72. Once this process is complete, the nominal energy to be delivered by capacitor 54 to patient 18 is displayed on the nominal energy display 46 of display panel 22, as indicated by the NOMINAL ENERGY DISPLAY block 88.

In the currently preferred embodiment, the operator then intervenes in the calibration process by applying the electrodes 30 of discharge paddles 16 to the terminals of meter 56. The operator then depresses discharge switch 32, to discharge the energy stored on capacitor 54 to meter 56, and reads the delivered energy in joules from meter 56. If the delivered energy does not equal the nominal energy selected, the operator uses the energy level increment and decrement switches 40 and 42 included on control panel 20 to increment or decrement the nominal energy appearing on energy display 46 of panel 22 so that it corresponds to the actual measurement of energy delivered. These steps are shown in FIG. 3 as the DELIVER TO METER, ENERGY TEST, and SET DELIVERED ENERGY blocks 90, 92, and 94, respectively.

In response to the information manually input to microprocessor 70 concerning the measured delivery of energy, microprocessor 70 determines the change in the voltage at capacitor 54 that is required to actually deliver the desired energy to a patient 18. This is accomplished at the ADJUST GAIN block 96 in the following manner. Assume that the capacitor 54 was intended to discharge 100 joules of energy but the energy delivered was measured as 98 joules. Because negative feedback is employed, the microprocessor 70 must then decrease the gain α of amplifier 64 to provide a larger voltage to capacitor 32.

In the preferred arrangement, a critically damped discharge is employed, in which the duration of the discharge is dependent upon the impedances of the various components of the circuit. Without information concerning the duration of the discharge or the transthoracic impedance of the patient, microprocessor 70 simply adjusts the gain α of amplifier 64 by an amount approximated to produce the desired nominal energy. For example, although the energy delivered by capacitor 54 is proportional to the square of its voltage, a piecewise linear approximation to this squared relationship between energy and voltage can be employed to determine the voltage and, hence, gain correction required to provide a discharge of the nominal 100 joules of energy selected.

In an alternative arrangement employing, for example, a truncated trapezoidal discharge, the duration of the discharge can be controlled and, thus, determined by microprocessor 70 independent of the characteristics of capacitor 54, paddles 16, and patient 18. Similarly, information concerning the transthoracic impedance of patient 18 can be obtained by microprocessor 70 from the ECG monitor 24. With this information, microprocessor 70 can be programmed to directly calculate the voltage and gain adjustments required to produce the nominal energy selected. For example, the relationship:

$$\text{Required Voltage} = \sqrt{2(ME)(R)/(DD)} \quad (1)$$

can be used to compute the required voltage, with ME being the energy measured by meter 78 in joules, R being the transthoracic chest impedance in ohms, and DD being the duration of the discharge in seconds. Assuming a transthoracic impedance of 50 ohms and a discharge period of 10 milliseconds, in the example illustrated above microprocessor 70 would employ equation (1) to determine that with 990 volts initially stored on capacitor 54 to produce the 98-joule discharge, 1000 volts would be required to produce the desired nominal energy discharge of 100 joules. Microprocessor 70 would then adjust the gain α of amplifier 64 downward, which value is stored in RAM 72, accordingly.

With the gain α adjusted, the program is returned to block 84 where the capacitor 54 is again charged to the nominal voltage. The process depicted by steps 86 through 96 is then repeated until the energy measured by meter 56 corresponds to the nominal energy selected and displayed on display 46 of panel 22. At that point, the program is exited at the ENERGY TEST block 92, causing microprocessor 70 to determine whether each of the nominal energy levels has been calibrated at the ALL LEVELS CALIBRATED? block 98. If they have not, the program is returned to block 84. Once each of the levels has been calibrated, however, the calibration mode of operation is exited at EXIT block 100. As will be appreciated, with meter 56 included as part of defibrillator 10, the entire process described above can be automatically performed by microprocessor 70. Alternatively, the meter 56 and a second computer or intelligence source can be employed independently of defibrillator 10 as part of an automated system in which the second computer monitors the energy measurements produced by meter 56 and applies that information to the system microprocessor 70 via a service port included in interface 76, allowing microprocessor 70 to calibrate each of the separate energy levels in the preceding manner.

Those skilled in the art will recognize that the embodiments of the invention disclosed herein are exemplary in nature and that various changes can be made therein without departing from the scope and the spirit of the invention. For example, although the embodiment described above relies primarily upon a microprocessor 70 to control the operation of defibrillator 10, embodiments employing hardware, rather than software, can be adopted. In addition, the manner in which the discharged energy is measured and used to correct subsequent discharges can be varied. For example, an arrangement employing positive, rather than negative, feedback could be adopted. Further, the parameters used to select and measure the magnitude of the discharge can be varied. Because of the above and numerous other variations and modifications that will occur to those skilled in the art, the following claims should not be limited to the embodiments illustrated and disclosed herein.

The embodiments of the invention in which an exclusive property or privilege is claimed are defined as follows:

1. A defibrillator for controlling the discharge of energy to a patient in response to an earlier measurement of energy discharged by the defibrillator, comprising:
   input means for allowing the measurement of energy to be input to said defibrillator; and
   control means for controlling the discharge of energy in response to the measurement of energy input to said defibrillator.

2. The defibrillator of claim 1, further comprising selection means, coupled to said control means, for selecting one of a plurality of energy levels for discharge by said defibrillator.

3. The defibrillator of claim 2, further comprising display means for displaying a quantity representative of said one of said plurality of energy levels selected.

4. the defibrillator of claim 3, wherein said input means comprises means for incrementing and decrementing said quantity displayed in response to the measurement of energy, said control means being for controlling the discharge of energy in response to said quantity displayed.

5. The defibrillator of claim 2, wherein said control means comprises means for comparing the measurement of energy with said one of said plurality of energy levels selected and controlling the discharge of energy in response thereto.

6. The defibrillator of claim 2, further comprising means for producing the measurement of energy, coupled to said input means.

7. The defibrillator of claim 6, wherein said control means is for automatically controlling the discharge of energy at each of said plurality of levels within some tolerance.

8. The defibrillator of claim 1, wherein said input means comprises means for providing a digital quantitative representation of the measurement of energy to said defibrillator.

9. A method of calibrating a defibrillator to produce a desired discharge of energy comprising the steps of:
   measuring a discharge of energy produced by the defibrillator;
   indicating to the defibrillator the discharge of energy measured; and
   adjusting subsequent discharge of energy in response thereto.

10. The method of claim 9, wherein the defibrillator allows one of a plurality of energy levels to be selected for discharge and wherein said step of measuring a discharge, said step of indicating to the defibrillator the discharge, and said step of adjusting subsequent discharges are each repeated for each one of said plurality of energy levels.

* * * * *